(12) United States Patent
Peckham (10) Patent No.: US 8,388,626 B2
(45) Date of Patent: Mar. 5, 2013

(54) METHODS OF EMPLOYING CALCIUM PHOSPHATE CEMENT COMPOSITIONS AND OSTEOINDUCTIVE PROTEINS TO EFFECT VERTEBRAE INTERBODY FUSION ABSENT AN INTERBODY DEVICE

(75) Inventor: Steven M. Peckham, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1344 days.

(21) Appl. No.: 11/594,475

(22) Filed: Nov. 8, 2006

(65) Prior Publication Data

US 2008/0109003 A1 May 8, 2008

(51) Int. Cl.
*A61B 17/56* (2006.01)
(52) U.S. Cl. .......................................... 606/94
(58) Field of Classification Search .............. 606/92–95; 623/17.11–17.16
See application file for complete search history.

(56) References Cited

U.S. PATENT DOCUMENTS

| | | | |
|---|---|---|---|
| 4,518,430 A | 5/1985 | Brown et al. | |
| 4,612,053 A | 9/1986 | Brown et al. | |
| 4,673,355 A * | 6/1987 | Farris et al. | 433/218 |
| 4,880,610 A | 11/1989 | Constantz | |
| RE33,161 E | 2/1990 | Brown et al. | |
| RE33,221 E | 5/1990 | Brown et al. | |
| 5,106,748 A | 4/1992 | Wozney et al. | |
| 5,149,368 A | 9/1992 | Liu et al. | |
| 5,152,836 A | 10/1992 | Hirano et al. | |
| 5,425,770 A * | 6/1995 | Piez et al. | 424/423 |
| 5,525,148 A * | 6/1996 | Chow et al. | 106/35 |
| 5,683,461 A * | 11/1997 | Lee et al. | 424/423 |
| 6,117,456 A | 9/2000 | Lee et al. | |
| 6,149,655 A * | 11/2000 | Constantz et al. | 606/94 |
| 6,224,629 B1 * | 5/2001 | Lin et al. | 623/16.11 |
| 6,294,187 B1 * | 9/2001 | Boyce et al. | 424/422 |

(Continued)

FOREIGN PATENT DOCUMENTS

EP 0835668 A1 4/1998
WO WO 96/14265 5/1996

OTHER PUBLICATIONS

Blom et al., "Transforming growth factor-B1 incorporation in a calcium phosphate bone cement: Material properties and release characterisitcs," John Wiley & Sons, Inc., J. Biomed Mater Res 59: pp. 265-272 (2002).

(Continued)

*Primary Examiner* — Kevin T Truong
*Assistant Examiner* — Christopher Beccia
(74) *Attorney, Agent, or Firm* — Sorell, Lenna and Schmidt LLP

(57) ABSTRACT

A minimal access method for mammalian vertebrae interbody fusion without the employment of an interbody device is described which comprises injecting a porous CaPC into an anterior portion of a disc space, and injecting an effective amount of fast-setting non-porous CaPC into an anterior portion of the disc space to rapidly produce a strong and stable interbody fusion without the employment of an interbody device. Methods are further described wherein at least one of the CaPCs comprises an effective amount of at least one osteoinductive protein. A minimal access method for vertebroplasty is described which comprises injecting an effective amount of a viscous non-porous CaPC into a vertebrae fracture channel to provide rapid stabilization and strength, and injecting a porous CaPC into trabecular bone space adjacent to the vertebrae fracture channel. Kits which relate to the methods of the present invention are described as well.

10 Claims, 2 Drawing Sheets

A.

B.

U.S. PATENT DOCUMENTS

| | | | |
|---|---|---|---|
| 6,348,055 B1* | 2/2002 | Preissman | 606/94 |
| 6,703,038 B1* | 3/2004 | Schaefer et al. | 424/426 |
| 6,929,692 B2* | 8/2005 | Tas | 106/690 |
| 7,052,517 B2* | 5/2006 | Murphy et al. | 623/23.51 |
| 7,135,027 B2* | 11/2006 | Delmotte | 606/93 |
| 7,153,307 B2* | 12/2006 | Scribner et al. | 606/93 |
| 7,172,629 B2* | 2/2007 | McKay | 623/23.61 |
| 7,238,209 B2* | 7/2007 | Matsuzaki et al. | 623/23.61 |
| 7,524,103 B2* | 4/2009 | McGill et al. | 366/189 |
| 7,544,196 B2* | 6/2009 | Bagga et al. | 606/93 |
| 7,547,317 B2* | 6/2009 | Cragg | 606/247 |
| 2003/0019396 A1* | 1/2003 | Edwards et al. | 106/35 |
| 2004/0022825 A1* | 2/2004 | Lagow | 424/423 |
| 2004/0034428 A1* | 2/2004 | McKay | 623/17.16 |
| 2004/0230309 A1* | 11/2004 | DiMauro et al. | 623/17.12 |
| 2006/0079905 A1* | 4/2006 | Beyar et al. | 606/76 |
| 2006/0148704 A1* | 7/2006 | Schense et al. | 514/12 |
| 2007/0098617 A1* | 5/2007 | Lagow | 423/305 |
| 2007/0184035 A1* | 8/2007 | Pugh et al. | 424/93.7 |
| 2008/0065088 A1* | 3/2008 | Hughes et al. | 606/93 |

OTHER PUBLICATIONS

Safdar et al., "Use of Osteopromotive Growth Factors, Demineralized Bone Matrix, and Ceramics to Enhance Spinal Fusion," Journal of the American Academy of Orthopaedic Surgeons, vol. 13, No. 2: pp. 129-137 (Mar./Apr. 2005).

Bohner, "Calcium Orthophosphates in medicine: from ceramics to calcium phosphate cements," International Journal of the Care of the Injured, vol. 31: pp. SD37-SD47 (2000).

Driessens et al, "Effective formulations for the preparation of calcium phosphate bone cements," Journal of Materials Science: Material in Medicine, vol. 5: pp. 164-170 1994.

Real et al., "In vivo bone response to porous calcium phosphate cement," Wiley Periodicals, Inc., J Biomed Mater Res 65A: 30-36 (2003).

Hing et al., "Characterization of porous hydroxyapatite," Journal of Materials Science: Materials in Medicine, 10:135 (1999).

* cited by examiner

METHODS OF EMPLOYING CALCIUM PHOSPHATE CEMENT COMPOSITIONS AND OSTEOINDUCTIVE PROTEINS TO EFFECT VERTEBRAE INTERBODY FUSION ABSENT AN INTERBODY DEVICE

FIELD OF THE INVENTION

The present invention provides minimal access methods for enhanced mammalian vertebrae interbody fusion and vertebroplasty which employ porous and non-porous calcium phosphate bone cements as well as at least one osteoinductive protein.

BACKGROUND OF THE INVENTION

Vertebrae interbody (spinal) fusion is a surgical procedure in which two or more vertebrae are joined or fused together. The objective of lumbar spine surgery, for example, is to stop the motion at a painful segment in the spine, thereby minimizing the pain and allowing the patient to increase their function. The theory is that if the joint does not move, the pain ceases. The fusion itself is achieved by creating a situation in which the body will try to repair itself by growing bone. As the bone grows between the two vertebral bodies, it fuses the painful joint together and eliminates the motion at that particular joint. In simplest terms a spinal fusion is a growing together of bone structures creating a solid bone bridge between vertebrae. Fusion surgeries typically require the use of bone graft to facilitate fusion. This involves taking small amounts of bone from the patient's bone (autograft), or from a donor (allograft), and then packing it between the vertebrae in order to "fuse" them together. This bone graft, along with a biomechanical spacer implant or interbody fusion device, will take the place of the intervertebral disc, which is partially or entirely removed in the process. Many state of the art cage technologies exist including those made of bone, titanium, polymer, and bioresorbable materials. Spinal fusion surgery is a common treatment for such spinal disorders as spondylolisthesis, scoliosis, severe disc degeneration, and spinal fractures, for example. Fusion surgery is generally considered only after extensive non-operative therapies have failed.

Three common fusion surgeries available include PLIF, ALIF and TLIF.

Posterior Lumbar Interbody Fusion (PLIF) concerns vertebrae access through an incision in the patient's back (posterior). The PLIF procedure generally involves MRI and CAT scans to determine what size interbody device (implant) the patient needs. Depending on the number of levels to be fused, a 3-6 inch incision is made in the patient's back and the spinal muscles are retracted (or separated) to allow access to the vertebral disc. The surgeon then removes the affected disc and surrounding tissue and prepares bone surfaces of adjacent vertebrae for fusion. Once the disc space is prepared, a bone graft or allograft, with an interbody device, is generally inserted into the disc space to promote fusion between the vertebrae. Additional instrumentation (such as rods or screws) may also be used at this time to further stabilize the spine.

Anterior Lumbar Interbody Fusion (ALIF) is similar to PLIF, however it is done from the front (anterior) of the body, usually through a 3-5 inch incision in the lower abdominal area or on the side. Once the incision is made and the vertebrae are accessed, and after the abdominal muscles and blood vessels have been retracted, the disc material is removed. The surgeon then inserts an interbody fusion device containing bone graft into the interbody space to stabilize the spine and facilitate fusion. Depending on the interbody device used and the condition being treated, additional instrumentation such as plates, rods and screws may also be used to further stabilize the spine.

Transforaminal Lumbar Interbody Fusion (TLIF) is a refinement of the PLIF procedure as a surgical treatment for conditions affecting the lumbar spine. The TLIF technique involves approaching the spine in a similar manner as the PLIF approach but generally more from the side of the spinal canal through an incision in the patient's back. This approach greatly reduces the amount of surgical muscle dissection and minimizes the nerve manipulation required to access the vertebrae, discs and nerves. The TLIF approach is useful for interbody fusion as it is generally less traumatic to the spine, is safer for the nerves, and allows for reduced access and endoscopic techniques to be used. As with PLIF and ALIF, disc material is removed from the spine and replaced with bone graft and an interbody fusion device inserted into the disc space. Instrumentation helps facilitate fusion while adding strength and stability to the spine.

A number of bone graft materials and interbody fusion devices may be used. The INFUSE® Bone Graft/LT-CAGE® Lumbar Tapered Fusion Device, for example, is a combination of an interbody device and an autograft replacement indicated for spinal fusion procedures in skeletally mature patients with degenerative disc disease (DDD) at one level from L4-S1, who may also have up to Grade I spondylolisthesis at the involved level. The INFUSE® Bone Graft/LT-CAGE® Lumbar Tapered Fusion Device is implanted via an anterior open or an anterior laparoscopic approach. INFUSE® Bone Graft, for example, represents a recombinant human bone morphogenetic protein-2 (rhBMP-2) formulation combined with a bovine-derived absorbable collagen sponge (ACS) carrier. To use INFUSE® Bone Graft, surgeons reconstitute the rhBMP-2 powder with sterile water and then apply it to collagen sponges. The sponges are inserted inside a pair of metallic cages, which are then implanted between the vertebrae. The thimble-like cages stabilize the spine and maintain the proper height between the vertebrae while fusion occurs.

The principal risk of these types of lower back surgery is that a solid fusion will not be obtained (nonunion) and further surgery to re-fuse the spine may be necessary.

Vertebroplasty is a minimally invasive, nonsurgical therapy used to strengthen a broken vertebra, for example, caused by a compression fracture. Vertebroplasty is generally accomplished by injecting polymethylmethacrylate (PMMA) cement into the vertebral body through a needle into the fractured bone. While PMMA has high mechanical strength, it cures fast and thus allows only a short handling time. Other potential problems of using PMMA injection include damage to surrounding tissues by a high polymerization temperature or by the unreacted toxic monomer, and the lack of long-term biocompatibility. Preissman U.S. Pat. No. 6,348,055, for example, reports that the use of syringes to deliver bone cement in vertebroplasty procedures. Preissman discloses using a screw-type high pressure injection device to provide an even injection pressure during delivery of the bone cement.

Calcium phosphate cements are conventionally prepared by mixing calcium phosphate powders of a special composition and a liquid, such as distilled water, for example, in a mortar to obtain kneaded cement which may then be filled into or applied to a defective portion of bone using a syringe or spatula, for example, and then allowed to cure. See, e.g., Mirtchi, et al., Calcium Phosphate Cements: Study of the beta-tricalcium Phosphate-Dicalcium Phosphate-Calcite Cements, *Biomaterials,* 11:83 (1990); F. C. M. Driessens, et al., *Bioceramics,* 10:279 (1997); K. S. TenHuisen, et al., Formation of Calcium-Deficient Hydroxyapatite from alpha-$Ca_3(PO_4)_2$, Biomaterials, 19:2209 (1998).

The bone regenerative properties of calcium phosphate cements (CaPCs) is improved, for example, by the addition of growth factors, such as recombinant human Transforming growth factor-beta1 (rhTGF-beta1). Blom E J, et al., *Transforming Growth Factor-Beta1 Incorporation in a Calcium Phosphate Bone Cement: Material Properties and Release Characteristics*, J Biomed Mater Res., 59(2):265 (2002). See, e.g., Khan, S. N., et al., *Use of Osteopromotive Growth Factors and Ceramics to Enhance Spinal Fusion*, J Am Acad Orthop Surg., 13(2):129 (2005); Ruhe P Q, et al., *Bone Inductive Properties of rhbmp-2 Loaded Porous Calcium Phosphate Cement, Biomaterials,* 25(11):2123 (2004); Sandhu, et al., *Spinal Fusion Using Bone Morphogenetic Proteins*, Orthopedics. 2004; July; 27(7):717-8.

A need, however, continues to exist for minimal access methods to effect strong and stable interbody fusions without the employment of interbody devices.

SUMMARY OF THE INVENTION

The present invention is directed to minimal access methods for mammalian vertebrae interbody fusion which comprise injecting a porous CaPC into an anterior portion of a disc space and injecting an effective amount of fast-setting nonporous CaPC into an anterior portion of the disc space to rapidly produce a strong and stable interbody fusion without the employment of an interbody device.

In addition, the current invention is directed to methods of enhancing mammalian vertebrae interbody fusion wherein at least one of the CaPCs comprises an effective amount of at least one osteoinductive protein. Methods are preferred at least one osteoinductive protein is selected from the group consisting of rhBMP-2, rhBMP-4, rhBMP-7, rhGDF-5 or heterodimers thereof.

The invention is further directed to a surgeon kit for vertebrae interbody fusion comprised of a container comprising a porous CaPC powder and a first mixing vessel, a non-porous CaPC powder and a second mixing vessel, and written instructions associated with the kit that indicate a method of injecting a porous CaPC and a non-porous CaPC for mammalian vertebrae interbody fusion without the employment of an interbody device. Kits are preferred which comprise instructions that indicate the injection of a majority of the porous CaPC prior to the injection of a majority of the non-porous CaPC. Kits are particularly preferred wherein at least one of the CaPC powders comprises an effective amount of at least one osteoinductive protein.

The invention is also directed to a minimal access method for vertebroplasty comprising injecting an effective amount of a non-porous CaPC into a vertebrae fracture channel to provide rapid stabilization and strength and injecting a porous CaPC into trabecular bone space preferably adjacent to the vertebrae fracture channel. Vertebroplasty can increase the patient's functional abilities, allow a return to the previous level of activity, and prevent further vertebral collapse. Preferred methods for vertebroplasty are wherein at least one of the CaPCs comprises an effective amount of at least one osteoinductive protein.

The invention is further directed to a surgeon kit for vertebroplasty comprised of a container comprising a porous CaPC powder and a first mixing vessel, a non-porous CaPC powder and a second mixing vessel, and written instructions associated with the kit that indicate a method of preparing the CaPC powders for vertebroplasty. Kits are preferred wherein at least one of the CaPC powders comprises an effective amount of at least one osteoinductive protein.

BRIEF DESCRIPTION OF THE FIGURES

FIG. 1. A. displays a top view of a human spinal vertebrae including the anterior body portion. B. displays a side view of a human spinal vertebrae including the anterior body portion.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Spinal fusion is a surgical method of treating degenerative disc disease after conservative treatments have failed. The procedure stabilizes the spine by fusing two adjacent vertebrae together and helps to alleviate the back pain caused by a degenerated disc in the spine. Interbody fusion implants generally include a load bearing body composed of one or more structural reinforcing members. Calcium phosphate material, calcium phosphate apatite for example, may be hardened around one or more structural reinforcing members of the interbody fusion implant for promoting fusion bone growth in the space between adjacent vertebrae. One object of the current invention, however, is to provide a method for interbody fusion of spinal vertebrae without the employment of an interbody device.

Methods described herein offer the advantage of a very minimal access approach. In a TLIF or PLIF approach, for example, a porous relatively slow setting cement, optionally containing at least one osteoinductive protein, is injected into the anterior portion of the disc space. This is followed by a fast setting nonporous cement to provide rapid stabilization. The key is controlling localization of the cement and ensuring sufficient filling of nonporous cement to provide adequate strength. Calcium phosphate cement (CaPC) hardens in situ to form solid hydroxyapatite, can conform to complex cavity shapes without machining, has excellent osteoconductivity, and is able to be resorbed and replaced by new bone. Both cements for use in methods described herein can be mixed with osteoinductive protein. The porous CaPC provides short term availability of the protein and initial bone formation. The nonporous CaPC provides access to the protein over a longer time as it is remodeled by the body.

As used herein the term non-porous calcium phosphate bone cements refer to cements that comprise up to 20-30% porous cement or cements that have only micron or sub-micron noninterconnected pores.

As used herein the term "injecting" refers to in vivo localization of a calcium phosphate cement, e.g., into an anterior portion of a disc space or into a fracture of a vertebrae, by means of a syringe, including but not limited to the employment of different gauge needles. For example, a vertebroplasty needle is typically 11 G-13 G while CaPC can go through needles as small as 16-18 G depending on the material.

Figure 1:
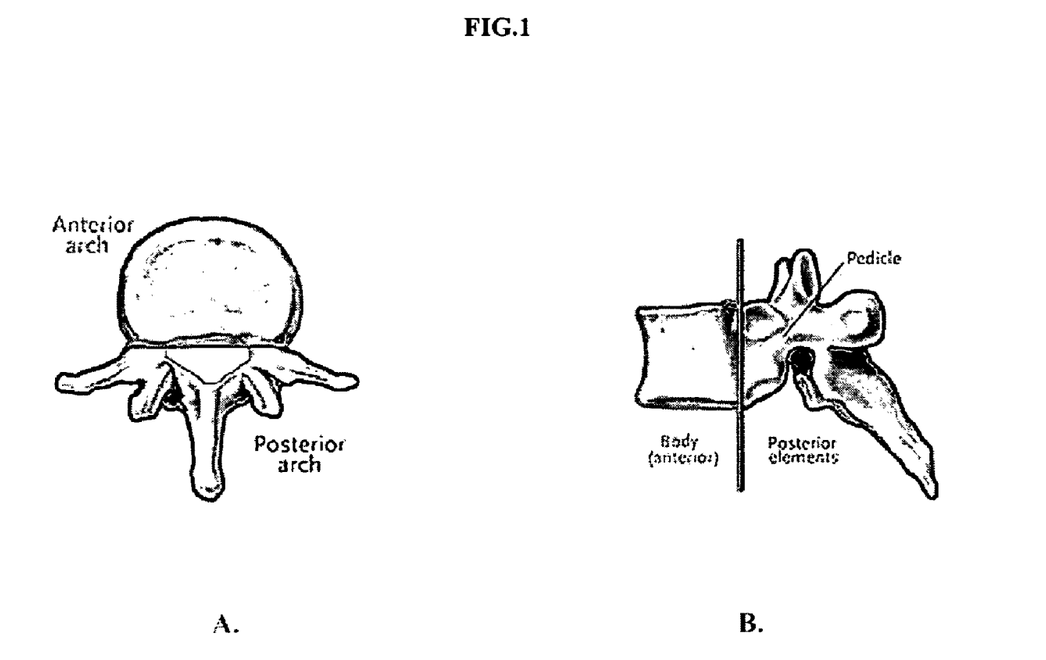

As used herein the term "anterior portion of a disc space" refers to the space generally occupied by a disc in a mammalian spine. See, FIGS. 1 and 2. FIG. 1A, for example, displays a top view of a human spinal vertebrae including the anterior body portion. FIG. 1B displays a side view of a human spinal vertebrae including the anterior body portion. Each vertebra has an anterior arch and a posterior arch, which form a hole, called a foramen. The spinal cord passes through foramen of each vertebra. The anterior arch is called the vertebral body. Discs connect one vertebral body to another to allow motion of the spine and cushion it against heavy loads. Together, the vertebral bodies and discs bear about 80 percent of the load to the spine.

Figure 2:
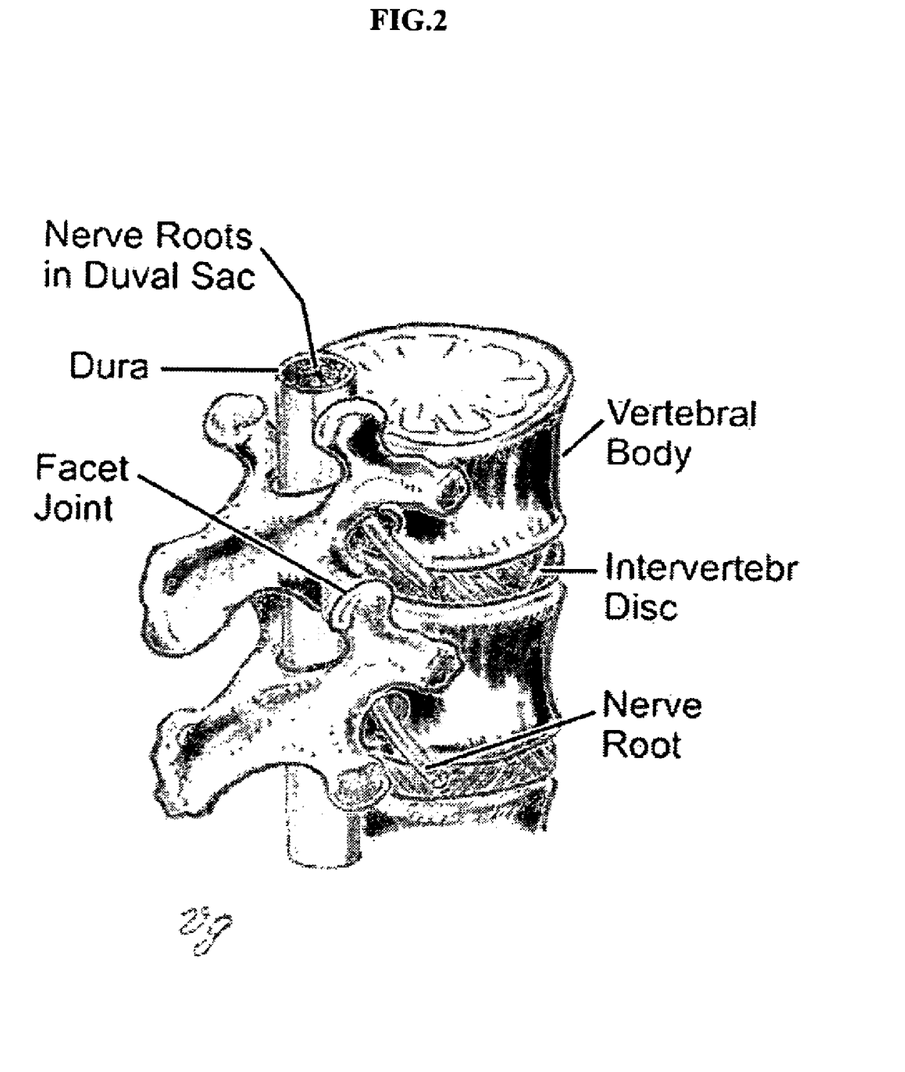
FIG. 2 shows a side view of a portion of a human spinal column including vertebrae and discs which occupy the disc space.

FIG. 2 shows a side view of a portion of a human spinal column including vertebrae and discs which occupy the disc space. The posterior arch consists of the pedicles, laminae, and processes. The pedicles are two short cylinders of bone that extend from the vertebral body. Nerve roots branch off the spinal cord and exit to the body between the pedicles of two vertebrae. If the spine becomes unstable, the pedicles may compress the nerve root, cause pain or numbness.

Bone and Hydroxyapatite:

Bone is a natural composite material, which by weight contains about 60% mineral, 30% matrix and 10% water. The mineral component of bone is a form of calcium phosphate known as hydroxyapatite (HA). Stoichiometric HA has the formula $Ca_{10}(PO_4)_6(OH)_2$.

Bone exists as compact or cortical, and cancellous or trabecular (also known as spongy) bone. Compact bone is very dense, consisting of parallel cylindrical units (osteons), and is found in the shafts of the long bones as well as on the outer surface of the smaller bones in the body. Compact bone has a compressive strength in the longitudinal direction (parallel to the long axis) ranging from 131-224 MPa. Trabecular bone is less dense and is made up of an array of rods and struts that form an open-cell foam, the pores of which are filled in by marrow.

When damaged, bone demonstrates a remarkable capacity for regeneration which can be simplified into three stages: inflammation, repair, and remodeling. Remodeling is accomplished through a process of resorption and deposition. This remodeling process is ongoing throughout the lifetime of a mammal. The space is invaded by osteoblasts and a blood vessel to supply nutrients.

Calcium Phosphate (CaP) Materials:

Calcium phosphate (CaP) materials have been used extensively for bone replacement and augmentation due to their similarity to the mineral component of bone. CaP materials are non-toxic, biocompatible, and exhibit bioactive behavior, being integrated into the tissue by the same processes active in remodeling healthy bone. This leads to osseointegration.

Calcium phosphates (CaPs) can be broadly classified into two categories, those that are obtained by high temperature processes and those that can be obtained through basic solution chemistry at ambient temperatures.

High temperature CaPs are those that form in the $CaO$—$P_2O_5$—$H_2O$ system at temperatures exceeding 500° C., including a- and b-tricalcium phosphate (a-TCP, b-TCP) as well as $Ca_3(PO_4)_2$, both widely used as bone substitutes in the form of powders, granules, or blocks. This category of CaPs also include Hydroxyapatite (HA) ($Ca_5(PO_4)_3OH$), a highly crystalline osteoconductive material which is the most stable CaP at neutral pH and the most prevalent form of CaP on the market. Biphasic calcium phosphate (BCP), a composite of HA and b-TCP is more soluble than pure HA. Tetracalcium phosphate (TTCP) ($Ca_4(PO_4)_2O$) and oxyapatite (OXA), $Ca_{10}(PO_4)_6O$ (a decomposition product of HA) are also in this class of CaPs.

Low temperature CaPs include monocalcium phosphate monohydrate (MCPM), dicalcium phosphate and dicalcium phosphate dihydrate (DCP, DCPD) ($CaHPO_4$ and $CaHPO_4.2H2O$), octocalcium phosphate (OCP) ($Ca_8H_2(PO_4)_6.5H2O$)

Calcium Phosphate Cements (CaPCs):

Calcium phosphate cements are conventionally prepared by mixing calcium phosphate powders of a special composition and a liquid, such as distilled water, for example, in a mortar to obtain kneaded cement which may then be filled into or applied to a defective portion of bone using a syringe or spatula, for example, and then allowed to cure. See, e.g., Mirtchi, et al., Calcium Phosphate Cements: Study of the beta-tricalcium Phosphate-Dicalcium Phosphate-Calcite Cements, *Biomaterials*, 11:83 (1990); F. C. M. Driessens, et al., *Bioceramics*, 10:279 (1997); K. S. TenHuisen, et al., Formation of Calcium-Deficient Hydroxyapatite from alpha-$Ca_3(PO_4)_2$, Biomaterials, 19:2209 (1998).

Commercially available CaPCs for use in methods described herein include but are not limited to, for example, BONESOURCE®, NORIAN SRS®, BIOBON®, CALCIBON®, AND CEMENTEK®. Such cements are described in U.S. Pat. No. 4,612,053; U.S. Pat. No. 5,149,368; U.S. Pat. No. 4,518,430; WO 96/14265; EP 1 296 909 A1, and EP 0 835 668 A1; which are incorporated herein by reference. Ca/P ratio varies between 1.5 and 1.67 most calcium phosphate cements. Bohner, M., *Calcium Orthophosphates in Medicine: From Ceramics to Calcium Phosphate Cements, Injury, International Journal of the Care of the Injured*, 31:SD37 (2000).

A calcium phosphate cement (CaPC) usually consists of a powder and a liquid phase. The powder phase may be an equimolar mixture of TTCP and DCPA, for example, or mass fractions of 0.729 of TTCP and 0.271 of DCPA, for example. CaPC mixtures containing tetracalcium phosphate (TTCP) (Ca4(PO4)2O), and dicalcium phosphate anhydrous (DCPA) ($CaHPO_4$), or TTCP and dicalcium phosphate dihydrate are example compositions for employment in methods described herein. When mixed with water these compositions rapidly form hydroxyapatite (HA) ($Ca_5(PO_4)_3OH$).

Because the particle size of the cement ingredients plays an important role in the setting and final properties of the cement, TTCP is ground to a median particle size of approximately 17 μm, for example. Commercial reagent grade DCPA is ground to a median particle size of about 1 μm, for example. It is proven essential to grind each solid component individually to the desired particle sizes. The two components are then thoroughly mixed and the resulting CaPC powder can be stored in a desiccator.

The liquid phase can be water, saline or other physiological fluids, for example. A phosphate containing solution is used as the liquid for a shorter hardening time, 5 min., for example. For applications requiring longer working times, a non-aqueous but water-miscible liquid such as glycerine or polyethylene glycol can be used. Ready-to-use premixed CaPC pastes are also prepared with these non-aqueous liquids. Because the cement setting reaction does not occur to a significant extent in these liquids, the cement would remain pliable for an indefinite period and harden after being placed in a defect and a sufficient amount of water diffusing from the surrounding tissues into the paste. Addition of a jelling agent such as hydroxypropyl methlycellulose, carboxyl methylcellulose, chitosan, and/or similar agents, to the cement liquid can improve the washout resistance of the cement paste before hardening occurs, allowing CaPC to harden in standing water. Chitosan is also be used to prepare CaPC materials that are less brittle and non-rigid. K. Ishikawa, et al., Properties and mechanism of fast-setting calcium phosphate cements, J. Mater. Sci. Mater. Med. 6, 528 (1995); A. Sugawara, et al., An in vitro evaluation of sealing ability of a calcium phosphate root canal sealer-filler, J. Endodont. 16(4), 162 (1990); A. Sugawara, et al., A new biocompatible material: calcium phosphate cement—biomedical applications, Tokyo Shika Ishikai Zashi. 38, 348 (1990); S. Takagi, et al., Premixed calcium phosphate cement pastes, Transactions of the Sixth World Biomaterials Congress. (2000) p. 19.; A. Cherng, S., et al., Effects of hydroxypropyl methylcellulose and other gelling agents on the handling properties of calcium phosphate cement. J. Biomed. Mater. Res. 35, 273 (1997); S. Takagi, et al., Properties of a non-rigid resorbable calcium phosphate cement, Special Issue, abstract No. 373, J. Dent. Res. 78, 152 (1999).

Porous CaPCs:

Injecting a "porous CaPC" into an anterior portion of a disc space generally refers to the process of injecting recently mixed liquid-form (e.g., "paste", "mixture") cement in vivo by means of a syringe that will harden into a "porous CaPC" as otherwise defined herein. Although non-porous CaPC is generally injected separately in methods of the present invention, it is contemplated herein that porous and non-porous CaPCs (in the liquid form, of course) can be delivered, for example, by means of layering the corresponding mixtures in a single syringe or by the use, for example, of dual-cylinder syringe wherein one cylinder contains the porous CaPC and the other contains the non-porous CaPC.

Calcium Phosphate Cement formulations are generally described and reviewed in Driessens, F. C. M., et al., *Effective Formulations for the Preparation of Calcium Phosphate Bone Cements*, Journal of Materials Science: Materials in Medicine 5:164 (1994). See, also, J Neurosurg Spine, 4(2): 154 (2006).

The term "porous CaPC", as used herein refers to a CaPC that upon hardening in vivo exhibits macropores larger than about 50 microns in diameter, preferably larger than 100 microns in diameter. Preferred hardened porous CaPC substantially exhibits macropores between about 100 and about 400 microns in diameter. Generally 100-400 micron is considered a favorable environment for bone ingrowth.

More Water Generally Produces Porosity:

Calcium phosphate cement must be ground to fine particle size (1-20 µm) before use. The compressive strength of conventionally set calcium phosphate cement usually does not exceed 50 MPa. Because the setting of calcium phosphate cement is essentially a dissolution-precipitation reaction, it is controlled by the particle size of the reactants: finer particles will dissolve faster than the coarse ones. Calcium phosphate cement combines a powder and liquid to initiate the setting reaction. The powder dissolves and then re-precipitates in the form of a stronger, chemically modified product. The solid-to-liquid ratio determines the final properties of the set cement including its compressive strength. Once set, standard calcium phosphate cement is a brittle and micro-porous (typically its porous fraction is higher than 20 vol %). Importantly, calcium phosphate cement sets rapidly (usually in less than an hour) in near physiological solutions having pH=7-8 at body temperature (37° C.). Such setting conditions make this material an ideal carrier for bone-growth factors (discussed infra). In vivo experiments are reported to evaluate the resorption rate of a calcium phosphate cement (CaPC) with macropores larger than 100 µm. del Real R P, et al., In Vivo Bone Response to Porous Calcium Phosphate Cement, J Biomed Mater Res A.; 65(1):30 (2003).

CaPC biomaterial porosity greater than 100 µm is considered a requirement for proper vascularization and bone cell colonization of a CP scaffold. Hing, K. A., *Characterization of Porous Hydroxyapatite*, Journal of Materials Science: Materials in Medicine, 10:135 (1999). Porosity also improves fluid penetration of the material and in turn enhances its dissolution, which is an important characteristic of a CaPC since the solubility largely determines their properties in vivo. At physiological pH, the solubility of the various CPs is in the following order: MCP>TTCP>a-TCP>DCPD>DCP>OCP>b-TCP>CDHA>HA. It is evident then, that though HA is biocompatible and undoubtedly osteoconductive, it suffers from limited bioactivity due to its stability and hence extremely slow degradation rate in biological fluids. This hurdle is often overcome through the use of BCP, which combines the long-term stability of HA with the enhanced bioactivity and solubility of TCP. The ratio of the two phases can be varied to tailor the material to the required degradation properties of a given application, but is usually 60% HA and 40% b-TCP.

U.S. Pat. No. 6,117,456, for example, discloses the preparation of a highly resorbable cement of the name alpha-BSM marketed in Europe by Biomet-Merck under the name of BIOBON®. This cement consists of two powder components, (i) poorly crystalline calcium phosphate (major phase), and (ii) well-crystallized DCPD (Brushite, $CaHPO_4.2H_2O$). BIOBON® has a Ca/P molar ratio less than 1.50. Although it is major, poorly crystalline calcium phosphate component reacts quite rapidly (started within the first 24 hours, and continues with the passage of time) to form apatitic tricalcium phosphate ($Ca_9(HPO_4)(PO_4)_5OH$), the full resorption of the crystalline component takes significantly longer to take place. BIOBON® (or alpha-BSM) is kneaded with a simple saline solution to form its paste.

It is sometimes desired that bone cements and bone filler materials which harden or set have an interconnected porosity (macroporosity) throughout their structure after hardening. This interconnected porosity, if of sufficient pore size, allows for vascularization and tissue ingrowth to occur into the structure. Pores greater than 70 microns in diameter have been found to allow tissue ingrowth. This tissue ingrowth can be encouraged by coating or filling the pores with osteoinductive or osteoconductive factors such as bone morphogenic proteins (BMPs) discussed infra.

A porous cement is known in the art for example which has an interconnected porosity that is produced by mixing a calcium source and a phosphate source with a carbonate source and mixing this powdered component with a liquid component having an acid component. Particularly citric acid and sodium bicarbonate react to produce carbon dioxide during the setting of a calcium phosphate cement, thereby introducing macroporosity into the structure. See, e.g., United States Patent Application 20030019396, published Jan. 30, 2003, entitled Porous Calcium Phosphate Cement. The acid and the carbonate react to form carbon dioxide thereby producing an interconnected porosity in the normally solid self-hardening bone cement. The method requires only a relatively low weight percent of the acid and base to be mixed with the liquid and powder cement components. Calcium and phosphate sources may, for example, be selected from the group consisting of tetra-calcium phosphate, dicalcium phosphate, tricalcium phosphate and monocalcium phosphate. Calcium phosphate cements of the type taught in Brown and Chow, U.S. reissued Pat. No. RE 33,161 and U.S. Pat. No. RE 33,221 and in Chow and Takagi U.S. Pat. No. 5,525,148 and in Constantz U.S. Pat. No. 4,880,610, the teachings of which are incorporated herein by reference. The chosen calcium and phosphate sources must self-set when coming into contact with an aqueous solution. This requires a combination or more calcium and/or phosphate sources. Thus, one source may be calcium alone or phosphate alone or one source may be a compound having both calcium and phosphate. The preferred ratio of acid to carbonate to produce a neutral pH has been found to be about 0.7 grams of acid to about 1.0 grams of carbonate. The preferred ratio of the acid and carbonate to the combined powdered and liquid components forming the calcium phosphate cement is about 10 to 20% by weight. Acids may be at least one, for example, selected from citric acid, malic acid, fumaric acid, lactic acid, succinic acid and orthophosphoric acid.

Non-Porous CaPCs:

Reducing the number of pores during setting, for example, increases the strength. Ideally, the compressive strength of non-porous CaPCs for employment in methods of the present invention should be above 100 MPa, close to the average strength of human cortical bone. Such strong cements may replace bone in critical load-bearing sites such as the vertebrae of human spine. An example factor to obtaining this strength, due to reduced porosity, is the addition of a small amount of tri-sodium citrate, for example, to the otherwise conventional mix.

Biocement D (Merck Biomaterial, Darmstadt, Germany), for example, after setting, generally exhibits pores smaller than 1 micron.

CALCIBON® calcium phosphate cement commercially available on the market (produced and marketed by Biomet-Merck) with a Ca/P molar ratio of 1.55, and it consists of a mixture of alpha-TCP (58-60 wt %), DCPA. (26-27 wt %), $CaCO_3$ (12-13 wt %), and HA (2%). It has a compressive strength over the range of 50-60 MPa, and in the bulk form (i.e., without any significant macroporosity).

U.S. Pat. No. 5,152,836 describes a calcium phosphate cement (again with a Ca/P molar ratio slightly greater than 1.50) composed of alpha-TCP (75 wt %), TTCP (18 wt %), DCPD (5 wt %), HA (2 wt %), kneaded into a paste with a relatively concentrated aqueous solution of chondroitin sulphate and sodium succinate. This cement has been in the market under the commercial name of BIOPEX® (Mitsubishi Material Co.) to achieve a compressive strength of 60 to 90 MPa.

Ca/P molar ratio may range, for example, from about 1.3 to about 1.5, preferably 1.35 to 1.45, and about 1.37 to about 1.42, e.g. 1.38 to about 1.4. One component, for example may be bi-phasic alpha-TCP ($Ca_3(PO_4)_2$, 95 wt %)+HA ($Ca_{10}(PO_4)_6(OH)_2$, 5 wt %) powder, while the second component is single-phase DCPD ($CaHPO_4.2H_2O$) powder. A setting solution ($Na_2HPO_4.2H_2O$) is used to form a self-setting calcium phosphate cement from the powder mixture. This cement can be used as bone filler or bone substitute in applications. See, e.g., Tas U.S. Pat. No. 6,929,692. The calcium phosphate cements of the present invention should be essentially non-porous, i.e. micron or submicron noninterconnected pores may be present but no macro porosity should be present in order to have increased strength.

Minimal Access without the Employment of an Interbody Device:

A preferred method of the present invention for mammalian vertebrae interbody fusion without the employment of an interbody device comprises injecting a porous CaPC into an anterior portion of a disc space and very soon thereafter, e.g., within about an hour, injecting an effective amount of fast-setting non-porous CaPC into an anterior portion of the disc space to rapidly produce a strong and stable interbody fusion. CaPCs which exhibit the properties described herein for use in the methods of the present invention are well known in the art.

Methods of the present invention are preferred wherein at least one of the CaPCs comprises an effective amount of at least one osteoinductive protein.

In some embodiments, the osteoinductive proteins or compositions used in this invention comprise a therapeutically effective amount to stimulate or induce bone growth of a substantially pure bone inductive or growth factor or protein in a pharmaceutically acceptable carrier. The preferred osteoinductive factors are the recombinant human bone morphogenetic proteins (rhBMPs). Most preferably, the bone morphogenetic protein is a rhBMP-2, rhBMP-4, rhBMP-7, or heterodimers thereof. rhBMP-2, for example, has been studied more than any other BMP and is FDA approved for use in certain spinal and tibial surgeries. See, e.g., Khan, S. N., et al., *Use of Osteopromotive Growth Factors and Ceramics to Enhance Spinal Fusion*, J Am Acad Orthop Surg., 13(2):129 (2005).

Osteoinductive proteins may be selected, for example, from the following group of substances: a) bone morphogenetic proteins, preferably BMP2, BMP4 or BMP7. Proteins that may enhance bone formation are also contemplated. Such proteins include b) growth factors, preferably TGFb-3 (transforming growth factor) or IGF-1 (insulin-like growth factor).

The bone regenerative properties of calcium phosphate cements (CaPCs) is improved, for example, by the addition of growth factors, such as recombinant human Transforming growth factor-beta1 (rhTGF-beta1). Blom E J, et al., *Transforming Growth Factor-Beta1 Incorporation in a Calcium Phosphate Bone Cement: Material Properties and Release Characteristics*, J Biomed Mater Res., 59(2):265 (2002). CaPC was studied through an assessment of its compressive strength and setting time, as well as its crystallinity, calcium-to-phosphorus ratio, porosity, and microscopic structure. Standard CaPC was prepared by mixing calcium phosphate powder (58% alpha-tricalcium phosphate, 25% anhydrous dicalcium phosphate, 8.5% calcium carbonate, and 8.5% hydroxyapatite) with a liquid (3 g/mL). The liquid for standard CaPC consisted of water with 4% disodium hydrogen phosphate, whereas the liquid for modified CaPC was mixed with an equal amount of 4 mM hydrochloride with 0.2% bovine serum albumin.

Ruhe P Q, et al., Bone Inductive Properties of rhbmp-2 *Loaded Porous Calcium Phosphate Cement, Biomaterials*, 25(11):2123 (2004). Osteoinductive properties of porous calcium phosphate (Ca—P) cement loaded with bone morphogenetic protein 2 (rhBMP-2) were evaluated. Histological analysis revealed excellent osteoconductive properties of the Ca—P material. Ruhe P Q, et al., reported conclusively that (1) Porous Ca—P cement is an appropriate candidate scaffold material for bone engineering, and (2) Bone formation can be enhanced by lyophilization, for example, of rhBMP-2 on the cement.

Posterior and anterior interbody fusions, for example, have been performed in several animal models that demonstrated the osteoinductive effects of BMP. Sandhu, et al., studied a sheep model of anterior lumbar interbody fusion with a threaded cage filled with either autograft or rhBMP-2 in a collagen carrier and reported a threefold increase in fusion with rhBMP-2. *Spinal Fusion Using Bone Morphogenetic Proteins*, Orthopedics, 27(7):717 (2004). Magin, et al., performed PLIF with monosegmental instrumentation and autograft, hydroxyapatite, or rhBMP-7 (rhOP-1) in 33 sheep. Fusion was not successful in the animals treated with hydroxyapatite, whereas all fusion was successful in sheep treated with rhBMP-7. Spine. 2001 Mar. 1; 26(5):469-78.

INFUSE® Bone Graft is the first autograft replacement approved for use in spinal fusion. The active ingredient in INFUSE® Bone Graft is recombinant human bone morphogenetic protein-2 (rhBMP-2). INFUSE® Bone Graft is used in an Anterior Lumbar Interbody Fusion (ALIF) procedure in combination with a metallic cage implant.

Dosage:

Although 0.05 mg osteogenic protein(s) (BMP, for example)/g of dry cement powder, for example, is an amount sufficient to heal bone defects the dose of osteogenic protein required to effect osteoinduction is generally more. Accordingly about 0.1 mg to about 3 mg BMP, for example/g of dry cement is a preferred range. One example embodiment of the present invention comprises between about 2 mg and about 3 mg per gram (/g), e.g., about 2.5 mg protein/g of dry cement powder As osteogenic proteins, BMPs for example, are rapidly degraded once released from the site of implantation, an important strategy has been to prolong the duration of secretion of BMP.

Recombinant hBMP-2, for example, can be used at a concentration of about 0.4 mg to about 4 mg per cc of prepared cement, preferably near 1.5 mg/ml. However, any bone morphogenetic protein is contemplated including bone morphogenetic proteins designated as BMP-1 through BMP-18. BMPs are available from Genetics Institute, Inc., Cambridge, Mass., for example. The BMPs and genes encoding them may also be prepared by one skilled in the art as described in U.S. Pat. No. 5,187,076 to Wozney, et al.; U.S. Pat. No. 5,366,875 to Wozney, et al.; U.S. Pat. No. 4,877,864 to Wang, et al.; U.S. Pat. No. 5,108,922 to Wang, et al.; U.S. Pat. No. 5,116,738 to Wang, et al.; U.S. Pat. No. 5,013,649 to Wang, et al.; and U.S. Pat. No. 5,106,748 to Wozney, et al.

Potential carriers for the osteogenic composition include calcium sulphates, polylactic acids, polyanhydrides, collagen, calcium phosphates, hyaluronic acid, polymeric acrylic esters and demineralized bone. Ceramic blocks and granules are commercially available from Sofamor Danek Group, B. P. 4-62180 Rang-du-Fliers, France and Bioland, 132 Rou d Espangne, 31100 Toulouse, France. The carrier may be soaked in a solution containing the factor.

Surgeon Kit:

A surgeon kit is provided for mammalian vertebrae interbody fusion, without the employment of an interbody device, comprised of a container comprising a porous CaPC powder and a first mixing vessel, a non-porous CaPC powder and a second mixing vessel, and written instructions associated with the kit that indicate a method for mammalian vertebrae interbody fusion.

Method for Vertebroplasty:

A minimal access method is provided for vertebroplasty comprising injecting an effective amount of a non-porous CaPC into a vertebrae fracture channel to provide rapid stabilization and strength, and injecting a porous CaPC into trabecular bone space adjacent to the vertebrae fracture channel to preferably surround the channel. Methods are preferred wherein at least one of the CaPCs comprises an effective amount of at least one osteoinductive protein. A surgeon kit for vertebroplasty is further provided comprised of a container comprising a porous CaPC powder and a first mixing vessel, a non-porous CaPC powder and a second mixing vessel, and written instructions associated with the kit that indicate a method of preparing the CaPC powders for vertebroplasty. Kits are preferred wherein at least one of the CaPCs comprises an effective amount of at least one osteoinductive protein.

EXAMPLES

Example I 5 g of anhydrous calcium hydrogen phosphate, 4 g tetra-calcium phosphate, and 7 g of hydroxyapatite are separately ground for 30 minuets to get particle sizes of 1-10 μm. The finely ground powders are combined in a bowl. The powders, being in one bowl, are further combined with an 0.7 g sodium bicarbonate and 0.3 g of lactic acid. 5 mls of a 1:1 mixture of distilled water and saline is added to the powders. This slurry is hand mixed with a spatula by pressing the slurry against the sides of the bowl and continually spreading and recombining, thereby forming a flowable paste. The mixing process should last anywhere from 45 seconds to 60 seconds. At such time, 0.4 g of rhBMP-2 is added to the paste. Mixing is continued for another 15 seconds to 60 seconds. An effect amount of the flowable paste is removed from the bowl and placed into the barrel of a syringe having a 10 to 12 G needle. The flowable paste is injected into the anterior portion of a disc space or into a fracture of a vertebrae, wherein enough of the flowable paste is injected to treat a vertebral defect as a first cement treatment leaving enough physical space for a second vertebral cement treatment. After which, 6 ml of a fast setting calcium phosphate cement is placed into the barrel of a syringe having a 10 to 12 G needle. The fast setting cement is injected into the same anterior disc space or fractured vertebrae. Non-limiting examples of commercially available fast setting cements to use in the present invention are BONESOURCE®, NORIAN SRS®, BIOBON®, CALCIBON®, and the like.

Example II

The procedures of Example 1 are repeated in Example 2, save for the delivery method of both cements. The flowable paste and the fast setting cement are layered in same barrel of the syringe for successive delivery of both materials to a vertebral defect. 0.5 ml of the flowable paste comprising the osteo-inductive factor is placed in the barrel of the syringe followed by 0.5 ml of a commercial fast setting cement. Both materials are delivered into the anterior portion of a disc space or into a vertebral fracture.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. A minimal access method for mammalian vertebrae interbody fusion without the employment of an interbody device comprising:

injecting a porous CaPC into an anterior portion of a disc space, wherein the porous CaPC comprises an effective amount of at least one osteoinductive protein and injecting an effective amount of fast-setting non-porous CaPC comprising a phosphate liquid into an anterior portion of the disc space to rapidly produce a strong and stable interbody fusion without the employment of an interbody device, wherein the non-porous CaPC does not contain an osteoinductive protein, and wherein a majority of the porous CaPC is injected prior to injecting a majority of the non-porous CaPC.

2. A method according to claim 1, wherein the fusion is performed according to a procedure selected from the group consisting essentially of TLIF, PLIF, and ALIF.

3. A method according to claim 1 wherein the at least one osteoinductive protein is selected from the group consisting of recombinant human bone morphogenetic proteins or heterodimers thereof and growth factors.

4. A method according to claim 3 wherein the osteoinductive protein is selected from the group consisting of rhBMP-2, rhBMP-4, rhBMP-7, rhGDF-5 or heterodimers thereof.

5. A method according to claim 4 wherein the osteoinductive protein is present in the amount about 0.4 mg to about 4 mg per cc of prepared cement.

6. A method according to claim 5 wherein the osteoinductive protein is present in the amount about 1 mg to about 2.5 mg per cc of prepared cement.

7. A method according to claim 6 wherein the Bone Morphogenetic Protein (BMP) is BMP2.

8. A minimal access method for vertebroplasty comprising:
injecting an effective amount of a viscous non-porous CaPC into a vertebrae fracture channel to provide rapid stabilization and strength, wherein the viscous non-porous CaPC does not contain an osteoinductive protein and comprises a phosphate liquid; and
injecting a porous CaPC into trabecular bone space adjacent to the vertebrae fracture channel, wherein the porous CaPC comprises an effective amount of at least one osteoinductive protein, wherein a majority of the porous CaPC is injected prior to a majority of the non-porous CaPC.

9. A method according to claim 1, wherein the porous CaPC has a particle size of 1 to 20 μm before use.

10. A method according to claim 8, wherein the porous CaPC powder has a particle size of 1 to 20 μm before use.

* * * * *